(12) United States Patent
Ras et al.

(10) Patent No.: US 11,712,196 B2
(45) Date of Patent: Aug. 1, 2023

(54) SKIN SENSOR

(71) Applicant: KONINKLIJKE PHILIPS N.V., Eindhoven (NL)

(72) Inventors: Arnoldus Johannes Martinus Jozeph Ras, Mierlo (NL); Walter Hermans, Overpelt (BE); Pascal Jean Henri Bloemen, Eindhoven (NL); Babu Varghese, Eindhoven (NL)

(73) Assignee: KONINKLIJKE PHILIPS N.V., Eindhoven (NL)

( * ) Notice: Subject to any disclaimer, the term of this patent is extended or adjusted under 35 U.S.C. 154(b) by 498 days.

(21) Appl. No.: 16/759,402

(22) PCT Filed: Nov. 1, 2018

(86) PCT No.: PCT/EP2018/079961
§ 371 (c)(1),
(2) Date: Apr. 27, 2020

(87) PCT Pub. No.: WO2019/086584
PCT Pub. Date: May 9, 2019

(65) Prior Publication Data
US 2020/0323482 A1    Oct. 15, 2020

(30) Foreign Application Priority Data
Nov. 2, 2017   (EP) .................................. 17199740

(51) Int. Cl.
*A61B 5/00* (2006.01)
*A61B 5/1455* (2006.01)
(Continued)

(52) U.S. Cl.
CPC ............... *A61B 5/441* (2013.01); *A61B 5/00* (2013.01); *A61B 5/0075* (2013.01); (Continued)

(58) Field of Classification Search
CPC ......... A61B 5/441; A61B 5/00; A61B 5/0075; A61B 5/0077; A61B 5/1455; A61B 5/443;
(Continued)

(56) References Cited

U.S. PATENT DOCUMENTS

| 6,993,167 B1 | 1/2006 | Skladnev |
| 2003/0045799 A1 | 3/2003 | Bazin |

(Continued)

FOREIGN PATENT DOCUMENTS

| CN | 201230877 Y | 5/2009 |
| WO | 02/094097 | 11/2002 |
| WO | 2015/174163 | 11/2015 |

OTHER PUBLICATIONS

Synopsys, LightTools Features https://optics.synopsys.com/lighttools/lighttools-feature-details.html.
(Continued)

*Primary Examiner* — Eric F Winakur
*Assistant Examiner* — Abid A Mustansir

(57) ABSTRACT

The invention provides a system (1) comprising a sensor (100) for measuring a skin parameter, the sensor (100) comprising (i) a plurality of spatially separated light sources (110) configured to provide light source light (111), and (ii) a detector (120) configured at a first distance (d1) from each of the light sources (110), wherein the first distance (d1) is selected from the range of 5-80 mm, wherein the sensor (100) is configured to provide the light source light (111) with optical axes (OL) under an angle (α) relative to an optical axis (O2) of the detector (120) selected from the range of 10-80°, wherein the sensor (100) comprises at least three light sources (110), wherein the light sources (110) are configured to provide unpolarized light source light (111), wherein the sensor (100) further comprises (iii) a sensor opening (107) downstream of the light sources (110) and
(Continued)

upstream of the detector (120) for propagation of the light source light (111) out of the sensor (100) and for entrance of reflected sensor light (111) into the sensor (100), and (iv) a sensor window (150), of a material (151) transmissive for the light source light (111), configured downstream of the light sources (110), configured upstream of the sensor opening (107), and configured upstream of the detector (120) with a second distance (d2) to the sensor opening (107) of at least 3 mm.

19 Claims, 7 Drawing Sheets

(51) Int. Cl.
*G02B 5/02* (2006.01)
*G02B 15/02* (2006.01)
*G02B 27/18* (2006.01)

(52) U.S. Cl.
CPC .......... *A61B 5/0077* (2013.01); *A61B 5/1455* (2013.01); *A61B 5/443* (2013.01); *G02B 5/0278* (2013.01); *G02B 15/02* (2013.01); *G02B 27/18* (2013.01); *A61B 2562/02* (2013.01)

(58) Field of Classification Search
CPC .. A61B 2562/02; G02B 5/0278; G02B 15/02; G02B 27/18
See application file for complete search history.

(56) References Cited

U.S. PATENT DOCUMENTS

| | | |
|---|---|---|
| 2009/0222068 A1 | 9/2009 | Oberreiter |
| 2010/0246016 A1 | 9/2010 | Carlson |
| 2012/0226268 A1 | 9/2012 | Liu |
| 2013/0053701 A1 | 2/2013 | Wiest |
| 2013/0256505 A1 | 10/2013 | Gomi |
| 2014/0055661 A1 | 2/2014 | Imamura |
| 2014/0121479 A1 | 5/2014 | O'Connor |
| 2015/0223749 A1* | 8/2015 | Park .................. G01N 21/6486 600/476 |
| 2016/0057325 A1 | 2/2016 | Park |
| 2016/0061726 A1 | 3/2016 | Ness |
| 2016/0270665 A1 | 9/2016 | Kantor |
| 2018/0184967 A1* | 7/2018 | Yoshida ................. A61B 5/442 |
| 2020/0113441 A1 | 4/2020 | Varchese |

OTHER PUBLICATIONS

International Search Report and Written Opinion dated Jan. 21, 2019 for International Application No. PCT/EP2018/079961 Filed Nov. 1, 2018.

Synopsys, LightTools Features https://optics.synopsys.com/lighttools/lighttools-feature-details.html, Dated: Apr. 24, 2020.

* cited by examiner

SKIN SENSOR

CROSS REFERENCE TO RELATED APPLICATIONS

This application is the U.S. National Phase application under 35 U.S.C. § 371 of International Application No. PCT/EP2018/079961 filed Nov. 1, 2018, published as WO 2019/086584 on May 9, 2019, which claims the benefit of European Patent Application Number 17199740.6 filed Nov. 2, 2017. These applications are hereby incorporated by reference herein.

FIELD OF THE INVENTION

The invention relates to a system comprising a sensor for measuring a skin parameter, such as skin gloss. The invention further relates to a method for evaluation of a skin parameter, such as skin gloss.

BACKGROUND OF THE INVENTION

Analysis of the skin is known in the art. U.S. Pat. No. 6,993,167, for instance, describes a system for collecting, storing and displaying dermatological images for the purpose of monitoring and diagnosis of skin conditions and skin cancers, including melanoma. A hand-held unit illuminates a section of the patient's skin, and an imaging device generates imaging signals from light derived from a skin section. Pairs of light output ports in the hand-held unit are arranged such that their intensity distributions overlap at their half-intensity levels so that the resulting summation of their intensities has a flat central region. Three image stores are maintained, one for lesion images, one for "nearby skin" images, and one for reference-white images. The "nearby skin" images are used by the system software to automatically determine the skin/lesion border. The reference white images are used to set the dynamic range of the instrument and to compensate for lighting irregularities. Two images of the same lesion taken at different times may be displayed simultaneously so that changes in the lesion may be determined. The calibration system is designed so that image data taken on any of multiple machines built to the same specification will be corrected back to a common reference standard to ensure absolute accuracy in color rendition.

U.S. Pat. No. 6,993,167B1 describes a system for collecting, storing and displaying dermatological images for the purpose of monitoring and diagnosis of skin conditions and skin cancers, including melanoma. A hand-held unit illuminates a section of the patient's skin, and an imaging device generates imaging signals from light derived from a skin section. Pairs of light output ports in the hand-held unit are arranged such that their intensity distributions overlap at their half-intensity levels so that the resulting summation of their intensities has a flat central region. Three image stores are maintained, one for lesion images, one for "nearby skin" images, and one for reference-white images. The "nearby skin" images are used by the system software to automatically determine the skin/lesion border. The reference white images are used to set the dynamic range of the instrument and to compensate for lighting irregularities. Two images of the same lesion taken at different times may be displayed simultaneously so that changes in the lesion may be determined. The calibration system is designed so that image data taken on any of multiple machines built to the same specification will be corrected back to a common reference standard.

US2013/0053701 describes a dermatoscope in the form of a handheld device. The dermatoscope comprising a display which is arranged in or on a housing, for an image of the skin surface and/or of a structure of the skin surface which is recorded by a surface sensor of the dermatoscope, and a storing means for storing the images recorded by the dermatoscope.

US2014/0055661 describes an imaging apparatus including a lens optical system L, an imaging device N including a plurality of first and second pixels P1 and P2, and an arrayed optical device K, wherein: the lens optical system L includes a first optical region D1 which primarily passes therethrough light oscillating in a direction of a first polarization axis and a second optical region D2 which passes therethrough light oscillating in every direction; and the arrayed optical device K makes light having passed through the first optical region D1 incident on the first pixels P1 and makes light having passed through the second optical region D2 incident on the second pixels P2.

US2014/0121479 pertains to a device and method for imaging of a human foot including a transmissive sheet with an upper surface configured to accommodate a sole of the foot, a light source positioned below the sheet for emitting light toward the sheet, and an optical path controller in the sheet or coupled to the sheet for altering a path of the light causing internal reflection of the light toward a predetermined region of the foot. The image can be analyzed for a predetermined characteristic associated with a human patient, and determination made whether the characteristic in the image matches the patient. Brightness in the image can be analyzed for tissue moisture information.

US2010/0246016 describes a glass article having an anti-glare surface. The anti-glare surface has a distinctness-of-reflected image of less than 95, and a haze of less than or equal to 50%. In one embodiment, the glass article further includes a smudge-resistant surface disposed on the anti-glare surface. Methods of making the glass article and anti-glare surface are also described.

US2013/0256505 describes an imaging device including a lighting unit whose lighting directions to a subject are able to be switched, and a control unit that performs focus adjustment on the subject for every lighting directions to calculate evaluation values in accordance with focus states, and determines a direction in which a focus state becomes best as a lighting direction based on the evaluation values to capture the subject.

WO2015174163 describes an imaging device includes a camera 31, a light source 32, a polarizer 35 arranged between the camera 31 plus the light source 32 and an object 11, and a spatial light modulator 40A arranged between the polarizer 35 and the object 11 to control a revolution angle of an emitting light polarization plane relative to an incident light polarization plane.

WO02094097 describes a method of determining a boundary of a lesion on the skin. An image of an area of skin that includes a lesion is captured. An annular variance test is performed on pixels around the lesion. Based on the results of the annular variance test, either a seeded region growing method or a color clustering method is applied to the image to calculate a boundary of the lesion. The color cluster method may produce multiple selectable boundaries. Provision is also made for a lesion boundary to be manually traced.

US20030045799 describes a portable device for observing a typological characteristic of the body. For example, the device can be used to observe at least one characteristic of the appearance of the skin or the hair. The device can generate at least two images of the zone under examination. The images differ from each other as to a feature other than magnification and the intensity of the light source.

SUMMARY OF THE INVENTION

The appearance of skin is significantly influenced by the presence of a thin emulsified film on the skin surface. Sebum containing lipids from sebaceous glands and epidermal keratinocytes is mixed with sweat and other lipids from cosmetics and environment to form this emulsified film of refractive index higher than that of epidermis. Sebum causes the skin to look glossier due to higher Fresnel reflection and smooth air-sebum interface. Optimal balance between sebum production and requirements imparts a non-glossy and healthy feel to the skin and is dermatologically and cosmetically desirable. Glossy and oily skin is considered to be unaesthetic and unpleasant and often associated with various dermatological disorders such as seborrhea, acne and hormonal imbalance. In sebum deficit conditions, the skin is vulnerable to infections and it feels itchy, dry, and looks lusterless, erythematous, and scaly.

As a result, strategies to balance the needs of the skin to its optimal lipid requirements by controlling the sebum secretion rate and/or to monitor the skin condition using non-invasive optical devices and methods seem necessary.

For home use applications, in particular in an environment like a bathroom, the sensor is expected to be water proof and contamination free. This can be realized by using a transparent glass window that shields the whole illumination and detection optics. In skin sensors such as dermatoscopes, a glass window may be placed in contact with the skin. However, it appears that when a glass window is used in contact with the skin, the sensor signal will be dominated by the 'ghost spot' arising from the Fresnel reflections of the two interfaces of the glass window (air-glass and glass-air interfaces). This ghost spot does not carry any information from the sample (skin) and this is what we call as "unwanted reflections". For given illumination conditions, the ghost spot is expected to be more intense than the light reflected from the skin because of the higher reflection coefficient of the glass-air interface compared to the effective reflection resulting from the skin. In addition to this, the ghost spot from the glass can interfere and may overlap with the signal coming from the skin resulting in poor estimation of skin oil/gloss content.

Devices for measuring skin glossiness (or "skin glossiness") are known in the art. However, for (reliable) home use, such devices are not available. Further, present devices may suffer from undesired artefacts, such as specular reflections spots that may influence the reliability of a reflection measurement.

Hence, it is an aspect of the invention to provide an alternative device (herein further the more general term "system" is applied) and/or skin (gloss) sensing method, which preferably further at least partly obviate(s) one or more of above-described drawbacks. The present invention may have as object to overcome or ameliorate at least one of the disadvantages of the prior art, or to provide a useful alternative.

Surprisingly, it appeared that the use of an additional window at some distance of the skin, and configured between the skin and the detector, and configured at some distance of the skin, can substantially improve the reliability of the signal. Such window has essentially no optical function such as converging or diverging light rays, but is especially an essentially planar window.

Amongst others, the invention provides a system ("system" or "skin sensor system" or "sensor system") comprising a sensor for measuring a skin parameter, especially one or more of skin gloss, skin oiliness, and skin hydration, but optionally also for measuring a hair parameter, the sensor comprising (i) a plurality of spatially separated light sources configured to provide light source light, and (ii) a detector configured at a first distance (d1) from each of the light sources, wherein the first distance (d1) may in specific embodiments be selected from the range of at least 1 mm, such as at least 2 mm, like at least 5 mm, such as selected from the range of 5-100 mm, like especially 5-80 mm, wherein the sensor comprises especially at least three light sources, wherein the light sources are configured to provide unpolarized light source light, wherein the sensor further comprises (iii) a sensor opening downstream of the light sources and upstream of the detector for propagation of the light source light out of the sensor and for entrance of reflected sensor light (back) into the sensor, and (iv) a sensor window ("window"), of a material transmissive for the light source light, (the sensor window) configured downstream of the light sources, configured upstream of the sensor opening, and configured upstream of the detector with a second distance (d2) to the sensor opening, especially being at least 1 mm, such as at least 2 mm, like even more especially of at least 3 mm. Especially, the sensor is configured to provide the light source light with optical axes (OL) under an angle ($\alpha$) relative to an optical axis (O2) of the detector selected from the range of 10-80°.

The use of such system may allow an essentially fixed distance to the skin, essentially equal to the second distance. The sensor opening defines the distance of the skin to the sensor window. It appears that with such distances, especially when the distance is at least 3 mm between skin and sensor window, artefacts, such as ghost spots, are substantially reduced. This improves the reliability of the system. Further, the presence of the window may also allow use of the sensor in humid environments. Hence, a sensor window is provided that—during use—is not in physical contact with the skin under investigation with the system.

Especially, the system may be used to measure a skin parameter. Hence, the system may especially be configured to measure a skin parameter. Alternatively or additionally, the system may also be used to measure a hair parameter. Hence, the system may alternatively or additionally (also) be configured to measure a hair parameter. Alternatively or additionally, the system may also be used to measure a parameter of another part of the body, such for measuring a part of the eye ball or an oral cavity. Hence, the system may alternatively or additionally (also) be configured to measure a parameter of a part of the body not being the skin or hair.

Further, with such system it may be possible to quantitatively estimate skin gloss. The term "skin gloss" herein refers to gloss of the skin but may also refer to "skin oiliness". Hence, the term "skin gloss" herein may also be defined as "skin parameter especially selected from one or more of the group consisting of skin gloss and skin oiliness". The values that may be measured with the system as described herein may reflect skin gloss and skin oiliness, as skin gloss may be related to skin oiliness. Herein, the term "skin gloss" is sometimes used to indicate both skin gloss or skin oiliness. Hence, in embodiments the term skin gloss may refer to skin gloss or skin oiliness, or especially to skin gloss.

As indicated above, the invention provides a system comprising a sensor. The term "system" may refer to a single device, e.g. having its own housing, but may also refer to a plurality of functionally coupled devices, such as e.g. the sensor and a control system or a control system comprising device, such as a computer, a smartphone etc. In embodiments, the term "sensor" may also refer to a plurality of sensors.

Especially, the system comprises a housing, such as the system comprising a device comprising a housing. The sensor may essentially be contained by the housing. The housing may include a housing aperture. Such housing aperture may provide a field of view to the detector. Further, the housing with housing aperture may also provide the second distance, which may be defined as the distance between the housing aperture (i.e. the skin when the sensor is configured on the skin) and the detector (or the last optics, especially a lens, before the detector (when seen from the detector)). The second distance may also be indicated as the free working distance, and may be defined as the distance between the housing aperture and the detector, or, when optics are available, between the housing aperture and the last optics (seen from the detector in the direction of the aperture). Hence, the second distance may also be indicated as the distance during operation between the skin and the detector, or, when optics are available, between the skin and the last optics (seen from the detector in the direction of the aperture). The housing can be seen as a distance holder, as it defines a distance between the skin and the detector (or its last optics). Such optics are configured upstream of the detector; i.e. the detector is configured downstream of such (optional) optics. The second distance may be in the order of 10-45 mm, but may even be up to 200 mm. Hence, in embodiments the second distance may be selected from the range of 10-200 mm, such as 10-30 mm, or in the range of 40-80 mm.

The detector is configured to detect the reflected light. Hence, the detector detects the reflected light for imaging during (sequential) illumination by the (unpolarized) light sources. The detector essentially only detects polarized light, e.g. due to a polarizer upstream of the detector. An optical axis of the detector and an optical axis of the sensor may essentially coincide. Further, the optical axis of the sensor and a net optical axis of all light sources may essentially coincide (as the light sources may be configured symmetrically relative to the detector).

The light sources are especially configured such that they are at a first distance from the detector, which first distance is smaller than the (relevant) field of view (dimensions). Further, the plurality of light sources may especially include sets of two (or more) light sources that are configured equidistant to the detector. Such sets may be controlled independently. Further, the first distances are not necessarily equal for each of the light sources. Hence, the phrase "the detector configured at a first distance (d1) from each of the light sources" and similar phrases may also be interpreted as "the light sources configured at first distances (d1) from the light sources, wherein the first distances for each of the light sources may be identical, or wherein there are two or more different first distances". As indicated herein, the first distance may especially be selected from the range of 1-100 mm.

Especially, the first distance is a shortest distance between a light emitting surface of the light source and a detector area (or detector surface) of the detector. As shown in the Figures, the distance is especially measured in a plane parallel to the opening or aperture (cross-section) or perpendicular to the optical axis of the sensor.

Hence, the invention provides (in an aspect (also)) a system comprising a sensor for measuring a skin parameter, the sensor comprising (i) a plurality of spatially separated light sources configured to provide (unpolarized) light source light, and (ii) a detector configured at a first distance from each of the light sources, wherein in specific embodiments the sensor is configured to provide the light source light with optical axes under an angle of incidence ($\alpha$) selected from the range of 10-80°, wherein during operation the sensor is (to be) configured on the skin, with an aperture of a housing of the sensor on the skin, and to detect reflected light source light (which is reflected at the skin), wherein the sensor comprises at least three light sources, wherein the light sources are configured to provide visible light source light, wherein the visible light source light is unpolarized, and wherein the first distance is selected from the range of 10-80 mm, wherein the detector is configured to detect polarized light. The system may include further features as defined in the accompanying embodiments.

The system may include a memory, a processing device (or "processor" or "processor system" or "controller" or "control system"), a user interface, and an indication unit for indicating a sensed skin gloss value, such as a LED indicator (e.g. suitable for indicating different values by switching on 0–n LEDs in dependence of the sensed value, wherein n is the number of LEDs used for indicating a maximum sensed value, with n in general being equal to or larger than two, such as at least three) and/or a display.

Examples of user interface devices include a manually actuated button, a display, a touch screen, a keypad, a voice activated input device, an audio output, an indicator (e.g., lights), a switch, a knob, a modem, and a networking card, among others. Especially, the user interface device may be configured to allow a user instruct the device or apparatus with which the user interface is functionally coupled by with the user interface is functionally comprised. The user interface may especially include a manually actuated button, a touch screen, a keypad, a voice activated input device, a switch, a knob, etc., and/or optionally a modem, and a networking card, etc. The user interface may comprise a graphical user interface. The term "user interface" may also refer to a remote user interface, such as a remote control. A remote control may be a separate dedicate device. However, a remote control may also be a device with an App configured to (at least) control the system or device or apparatus.

The controller/processor and the memory may be any type. The processor may be capable of performing the various described operations and executing instructions stored in the memory. The processor may be an application-specific or general-use integrated circuit(s). Further, the processor may be a dedicated processor for performing in accordance with the present system or may be a general-purpose processor wherein only one of many functions operates for performing in accordance with the present system. The processor may operate utilizing a program portion, multiple program segments, or may be a hardware device utilizing a dedicated or multi-purpose integrated circuit.

The sensor comprises (i) a plurality of spatially separated light sources configured to provide light source light ("light"). Especially, the sensor comprises at least three spatially separated light sources.

The term "light source" may comprise a semiconductor light-emitting device, such as a light emitting diode (LEDs), a resonant cavity light emitting diode (RCLED), a vertical cavity laser diode (VCSELs), an edge emitting laser, etc. The term "light source" may also refer to an organic light-emitting diode, such as a passive-matrix (PMOLED) or an active-matrix (AMOLED). In a specific embodiment, the light source comprises a solid state light source (such as a LED or laser diode). In an embodiment, the light source comprises a LED (light emitting diode). The term LED may also refer to a plurality of LEDs. Further, the term "light source" may in embodiments also refer to a so-called chips-on-board (COB) light source. The term "COB" especially refers to LED chips in the form of a semiconductor chip that is neither encased nor connected but directly mounted onto a substrate, such as a PCB. Hence, a plurality of semiconductor light sources may be configured on the same substrate. In embodiments, a COB is a multi LED chip configured together as a single lighting module.

Further, the light sources are configured to provide unpolarized light source light. This allows the sensor derive information from the polarization direction of the reflected light. Hence, with the system, in specific embodiments unpolarized light source light is provided at the skin.

The light sources may be configured to provide one or more of visible light and infrared light (especially near infrared light). The visible light may be white light. The IR light may e.g. especially be radiation having a wavelength selected from the range of 750-3000 nm, such as selected from a range up to about 1200 nm.

Further, the light sources are especially configured to provide white light. The term white light herein, is known to the person skilled in the art. It may especially relate to light having a correlated color temperature (CCT) between about 2000 and 20000 K, especially 2700-20000 K, for general lighting especially in the range of about 2700 K and 6500 K, and for backlighting purposes especially in the range of about 7000 K and 20000 K, and especially within about 15 SDCM (standard deviation of color matching) from the BBL (black body locus), especially within about 10 SDCM from the BBL, even more especially within about 5 SDCM from the BBL. Especially, the white light may be provided by a blue LED with a yellow emitting luminescent material. Such light source can provide white light that is essentially not polarized. Visible light has a wavelength selected from the range of 389-780 nm.

Especially, the sensor comprises a plurality of spatially separated light sources. This implies that there is some distance between the light sources. Especially, the light sources are configured with the detector in between. Further, especially the maximum number of light sources is about twelve, such as ten, like eight, such as six or four or three. Up to about twelve, even more especially up to about eight, such as up to about six allows a configuration around the sensor which also allows a spatial separation between adjacent light sources which may (also) be in the order of about 1-100 mm, such as at least 5 mm, like at least 10 mm.

Hence, in embodiments the system comprises at least three light sources. In yet further embodiments, the sensor has a sensor optical axis, and the light sources are configured rotationally symmetric around the sensor optical axis. In embodiments, the light sources may be configured relative to each other under angles with the optical axis of 360°/n, wherein n is the number of light sources. Hence, in embodiments wherein the system comprises at least three or four light sources, the mutual angles with the optical axis may be 120° and 90°, respectively.

Therefore, as indicated above, the system comprise especially at least two light sources, even more especially at least three light sources, and the light sources are especially configured to provide unpolarized (visible) light source light, even more especially white light.

In embodiments, the system may especially comprise a plurality of light sources providing visible light source light, wherein the visible light source light is unpolarized, especially wherein essentially all visible light source light is unpolarized. Especially, each of the light sources provides essentially unpolarized visible light source light. Hence, these embodiments provide the skin with unpolarized light source light, wherein the light source light is essentially not partially polarized. Therefore, especially the light sources are configured to provide visible light source light, wherein the visible light source light is unpolarized.

As further indicated above, the system also comprises a detector configured at a first distance (d1) from each of the light sources. Good results were obtained with the first distance (d1) being in the range of about 1-80 mm. Hence, in specific embodiment the first distance may by be selected from the range of 1-80 mm, especially from the range of 2-60 mm, such as in the range of 5-80 mm, like especially 4-20 mm, such as 5-20 mm, like in the range of 6-14 mm. Hence, in embodiments the first distance (d1) may be selected from the range of about 4-20 mm, such as 6-14 mm, like especially about 8-14 mm.

Especially, the detector is configured to detect polarized light. To this end, the detector may comprises a polarizer, which is configured upstream of the detector. In this way, only polarized light, especially S-polarized light, may be received by the detector. Below, some specific embodiments of the polarizer are further elucidated.

Especially, the detector is configured to detect polarized light. Hence, the sensor may comprise a polarizer configured upstream of the detector. The polarizer may filter the reflected (unpolarized) light source light (reflected at the skin) such that the detector receives polarized light, especially S-polarized light, or alternatively especially P-polarized light.

In specific embodiments, the sensor is configured to provide the light source light with optical axes (OL) under an angle of incidence ($\alpha$), especially selected from the range of 10-80°, with the skin at a third distance (d3) and to detect reflected light source light (reflected at the skin). Of course, the skin is not part of the system. However, the system is especially configured to measure skin at a third distance. For instance, the system may include a distance holder or other element, which allows configuration of the sensor at the third distance. At this distance, the above indicated angle of incidence may be achieved, which is in the range of 10-80°, more especially 20-80°. In specific embodiments, which are further elucidated below, the angle is selected from the range of 20-60°.

Therefore, in specific embodiments the sensor is configured to provide the light source light with optical axes under an angle ($\alpha$) relative to an optical axis (O2) of the detector selected from the range of 10-80°. Further, in embodiments the angle ($\alpha$) may especially be selected from the range of 20-60°. The optical axis of the detector/of the sensor, is herein also indicated as "sensor optical axis".

Hence, in embodiments the sensor may especially be configured to detect reflected light source light, with the skin at a third distance (d3).

The distance holder is configured to be placed on the skin such that the skin is at a second distance to the detector or the last optics before the detector (seen from the detector). Especially, the distance holder may be configured to be placed flat on the skin such that the skin is at a second distance to the detector or last optics before the detector (seen from the detector). The distance holder may be comprised in a housing of the sensor. Especially, the system may comprise a housing at least partially enveloping the sensor, wherein the housing comprises the distance holder. Alternatively, the system may comprise a housing and a (separate) distance holder; in such embodiments the second distance may further be increased. Also a distance holder other than a housing may comprise an aperture.

The system, or at least part thereof, such as the housing, may be configured to be pressed on the skin. Hence, 'on the skin' may indicate that the system, or at least part thereof, is pressed against the skin (during use), especially wherein the distance holder, such as a housing, is pressed against the skin. Hence, the term "second distance" especially refers to the distance between the detector, or its last optics (seen from the detector), and the skin, during use of the system. The second distance is a non-zero distance between the aperture/skin and the detector (or optics upstream of the detector, when such optics are available). The term optics may especially refer here to a lens.

In embodiments, the sensor may comprise one or more of a silicon based sensor and an InGaAs based sensor.

In specific embodiments, the detector comprises a 2D camera, such as a CCD (or CMOS) camera TD-Next 5620 M7_1A and TD-Next 5640 M12_3B. Each pixel may essentially consist of three pixels for blue, green, and red, respectively. This may provide the detector blue, green, and red channels intensity separately.

In embodiments, the detector may have a detector area of about $10*10$ mm$^2$. The detector may have in the order of 1 Megapixel or more.

In further embodiments, the sensor may further comprise a focusing lens configured upstream of the detector (and downstream of the sensor window). The focusing lens may be configured to have at one side the detector in focus and/or at the other side of the lens the skin in focus. The lens may allow a good image of the skin at the detector.

In embodiments, the sensor may further comprise an aperture configured upstream of the detector and upstream of the focusing lens. This may further add to resolution. The aperture may in embodiments have a diameter selected from the range of 0.1-5 mm, more especially 0.1-2 mm, like especially 0.1-0.8 mm.

The optical axis of the system may be configured perpendicular to the detector. The optical axis of the light source may be defined as coinciding with a ray of light source light that is reflected at a mirror at distance d2 (such as the skin) and which reaches the detector after propagating through the center of the aperture (and reach an edge of the detector surface). Hence, the sensor is configured to provide the light source light with optical axes (OL) under an angle ($\alpha$) relative to an optical axis (O2) of the detector selected from the range of 10-80°. Angle $\alpha$ may thus also be defined as the angle of incidence. The perpendicular to the detector (surface) may essentially coincide with a perpendicular to mirror at distance d2 (such as the skin). The mirror and detector surface may be configured essentially parallel. Likewise, the aperture and detector surface (and mirror) may be configured essentially parallel. During use, the optical axis of the sensor (system) is thus configured essentially perpendicular to the skin (and the detector (surface)).

As indicated above, the sensor further comprises (iii) a sensor opening downstream of the light sources and upstream of the detector for propagation of the light source light out of the sensor and for entrance of reflected sensor light into the sensor. For instance, the system may include a wall with the sensor opening. The system may also include a distance holder or other element protruding from the system, which distance holder or other element allow arrangement of the skin to be sensed at a predefined distance from the sensor (and of the window; see below). To this end, the opening may have dimensions that prevent a substantial bulging of the skin into the sensor opening. Hence, by defining the sensor opening, the distance between skin and sensor and between skin and window can be defined.

Especially, the sensor opening is configured such, that the distance between skin and window is in the range of at least 1 mm, such as at least 2 mm, like even more especially of at least 3 mm.

Hence, the system also comprises a sensor window, configured downstream of the light sources, configured upstream of the sensor opening, and configured upstream of the detector with a second distance (d2) to the sensor opening of—in specific embodiments—at least 3 mm. As indicated above, the window is especially an essentially planar window. Further, especially the window is configured such that is does not allow entrance of water in the sensor through the window or at the edges of the window.

Further, the window is of a material transmissive for the light source light. Suitable light transmissive materials may comprise one or more materials selected from the group consisting of a transmissive organic material, such as selected from the group consisting of PE (polyethylene), PP (polypropylene), PEN (polyethylene napthalate), PC (polycarbonate), polymethylacrylate (PMA), polymethylmethacrylate (PMMA) (Plexiglas or Perspex), cellulose acetate butyrate (CAB), silicone, polyvinylchloride (PVC), polyethylene terephthalate (PET), including in an embodiment (PETG) (glycol modified polyethylene terephthalate), PDMS (polydimethylsiloxane), and COC (cyclo olefin copolymer). Especially, the light transmissive material may comprise an aromatic polyester, or a copolymer thereof, such as e.g. polycarbonate (PC), poly (methyl)methacrylate (P(M)MA), polyglycolide or polyglycolic acid (PGA), polylactic acid (PLA), polycaprolactone (PCL), polyethylene adipate (PEA), polyhydroxy alkanoate (PHA), polyhydroxy butyrate (PHB), poly(3-hydroxybutyrate-co-3-hydroxyvalerate) (PHBV), polyethylene terephthalate (PET), polybutylene terephthalate (PBT), polytrimethylene terephthalate (PTT), polyethylene naphthalate (PEN); especially, the light transmissive material may comprise polyethylene terephthalate (PET). Hence, the light transmissive material is especially a polymeric light transmissive material. However, in another embodiment the light transmissive material may comprise an inorganic material. Especially, the inorganic light transmissive material may be selected from the group consisting of glasses, (fused) quartz, transmissive ceramic materials, and silicones. Also hybrid materials, comprising both inorganic and organic parts may be applied. Especially, the light transmissive material comprises one or more of PMMA, transparent PC, or glass. Especially, the material is selected from the group consisting of glass and poly methyl methacrylate.

Further, the sensor window is especially transparent. Such window may have a relatively large mean free path for the wavelength of interest, such as the light source light wavelength(s). Hence, in embodiments the mean free path only taking into account scattering effects may be at least 5 mm, such as at least 10 mm for the light source light. The term "mean free path" is especially the average distance a ray will travel before experiencing a scattering event that will change its propagation direction.

It appears that short distances between the sensor window and the skin are relatively detrimental to the sensor signal, as the ghost spot may be relatively prominent. Especially, the second distance is at least 3 mm, even more especially at least 4 mm. In specific embodiments, the second distance (d2) is selected from the range of 4-10 mm. In such embodiments, the ghost spot may essentially not be observed by the detector.

Especially, the distance (d2) and the sensor window thickness (d4) of the sensor window are chosen such that direct specular reflections from the cover glass to the detector is avoided. For a predetermined sensor, the position of the skin (during use of the device) can be estimated or predicted, and thereby an optimal second distance (d2) and the thickness (d4) of the sensor window can be defined.

In embodiments, based on a predefined second distance d2, the sensor window thickness may be optimized (e.g. via simulations), and the sensor window with the optimized sensor window thickness may be arranged at a position such that the second distance d2 will be obtained (during use of the sensor).

Alternatively, in embodiments based on a predefined sensor window thickness, the second distance may be optimized (e.g. via simulations), and the sensor window with the optimized sensor window thickness can be arranged at a position such that the optimized second distance d2 will be obtained (during use of the sensor).

In further embodiments, based on a predefined second distance range and on a predefined sensor window thickness range, the sensor window thickness and sensor window position may be optimized (via simulations). The sensor window with optimized sensor window thickness can be arranged at a position such that the optimized second distance d2 will be obtained (during use of the sensor).

The sensor opening, downstream of the sensor window, may essentially have any (cross-sectional) shape. However, especially the sensor opening has one or more curved (cross-sectional) shapes, such as oval, even more is essentially circular. As indicated above, the sensor opening may not be too large. In specific embodiments, the sensor opening has an equivalent circular diameter selected from the range of 1-65 mm, such as especially 1-20 mm, like at least 3 mm. The equivalent circular diameter (or ECD) of an irregularly shaped two-dimensional shape is the diameter of a circle of equivalent area. For instance, the equivalent circular diameter of a square with side a is $2*a*SQRT(1/\pi)$. As indicated, the sensor opening may especially be round.

Good results are obtained with a window thickness in the range of about 0.1-20 mm. Therefore, in embodiments the sensor window has a sensor window thickness (d4) selected from the range of 0.1-20 mm, like in the range of about 1-10 mm. Especially, the thickness of the sensor window is essentially constant over the window.

By using the herein described conditions, the ghost spot is diminished or even essentially, leading to more reliable sensor results, e.g. as result of a higher signal/background ratio. Even better results can be obtained wherein the rays responsible for the ghost spot are scattered. Therefore, in specific embodiments the sensor window comprises a central part and a peripheral part, wherein the optical axis (O2) of the detector passes through the central part, and wherein the peripheral part comprises antiglare elements. The antiglare elements may include surface scattering features and/or bulk scattering features. The antiglare elements may include irregular or regular shaped structures on part of the surface of the sensor window and/or scattering particles in the window. Especially, the optical axes of the light sources also pass through the central part (i.e. the light source light collinear with the optical axes is not scattered by the antiglare elements. The central part does essentially not comprise such antiglare elements, and may thus be essentially transparent. The peripheral part is especially translucent.

Especially, the peripheral part (thus) surrounds the central part. Relative to a total area of the peripheral part and the central part, the former may be about 5-90% of the total area (of the sensor window), like 10-80%, such as 10-50%, and the latter may be about 10-95% of the total area, like 20-90%, such as 50-90%. Especially, in embodiments the area of the central part is about equal, or larger, than the area of the peripheral part. In other embodiments, however, the area of the central part is about equal, or smaller, than the area of the peripheral part.

Hence, in embodiments part of an outer surface of the window and/or part of a detector directed surface of the window may comprise structures (herein also indicated as "surface features") that provide surface roughness. These structures may be random shaped and/or regularly shaped. Further, these structures may be randomly arranged and/or regularly arranged. Therefore, in embodiments the sensor window comprises an upstream face and a downstream face, wherein one or more of the upstream face and the downstream face in the peripheral part has a root mean square surface roughness, especially selected from the range of 20-1000 nm, such as especially selected from the range of 40-500 nm.

In embodiments, the surface features may have an average cross-sectional equivalent circular diameter selected from the range of 40 nm-100 μm. Yet further an average distance between neighboring surface features is equal to or less than five times the average cross-sectional equivalent circular diameter. In a specific embodiment, surface features are arranged in a configuration complying with at least about 80% of the highest possible theoretical packing, like at least 90% of the highest possible theoretical packing. For instance, assuming surface features having essentially circular cross-sections, a closest packing may be obtained with a hexagonal arrangement of the surface features, which could essentially lead to 100% of the highest possible theoretical packing. The highest possible theoretical packing is lower than 100%, unless surface features would be used that completely match with each other, like cubes with identical cross-sectional shapes (parallel to a plane of the window).

In specific embodiments, the system may further comprise an analysis system. The analysis system is configured to generate a corresponding skin sensor value in dependence of a sensor signal of the sensor. The analysis system and sensor may be incorporated in a single device, such as skin cleansing device, skin rejuvenation device, etc. Hence, in embodiments the system comprises a skin care device, like such skin cleansing device, skin rejuvenation device, etc., wherein the skin care device comprises the sensor and the analysis system. The analysis system can translate the signal of the sensor, more especially of the detector, into a signal that may contain useful information of the user, such as an indication of the skin glossiness on an indicator unit (such as a display or LED bar). The skin sensor value can be the skin parameter of may be further processed into the skin parameter based on predefined relations between the skin sensor value and the skin parameter.

In other embodiments, however, the sensor may be comprised by a separate device, that is wired or wireless coupled to an analysis system. For instance, such analysis system may be comprised by a smartphone. For instance, an App may be used to readout the sensor and display a skin sensor value based on the sensor signal generated by the sensor.

Therefore, in yet other embodiments the system comprises (i) a skin care device, wherein the skin care device comprises the sensor, and (ii) a second device functionally coupled to the skin care device, wherein the second device comprises the analysis system. The term "analysis system" may also refer to a plurality of interrelated systems. For instance, the sensor may (further) comprise a processor and an external device may comprise a processor which may communicate with each other. The processor of the sensor may provide the sensor signal, and the processor of the external device generates on the basis thereon the skin sensor value, indicative of the glossiness/oiliness of the skin.

The sensor signal may be the detector signal. In other embodiments, the sensor signal may be a processed detector signal. Hence, the phrase "base on the detector signal" may in embodiments also refer to a processed detector signal. Based on the sensor signal, i.e. essentially based on the detector signal, the analysis system may provide a corresponding skin sensor value.

When the system comprises a functional device, such as a skin cleansing device or skin rejuvenation device, the device may be configured to execute an action in dependence of the sensor signal of the sensor (for sensing gloss) (or skin sensor value). For instance, when a certain lower or upper threshold of skin gloss (or skin oiliness) is reached, the functional device may provide a signal to the user, like a sound or vibration signal. Alternatively or additionally, the functional device may reduce or increase specific actions in dependence of the sensor signal, such as in increased or reduced massaging of the skin in dependence of the sensor signal.

The terms "upstream" and "downstream" especially relate to an arrangement of items or features relative to the propagation of the light from a light generating means (here the especially the light source), wherein relative to a first position within a beam of light from the light generating means, a second position in the beam of light closer to the light generating means is "upstream", and a third position within the beam of light further away from the light generating means is "downstream". When light is reflected to the sensor, the light ray propagates from the skin to the detector. Hence, with respect to the detector, essentially any element between the sensor window and detector is upstream of the detector; relative to the light source, any element between light source and sensor window, or between light source and skin, is downstream of the light source. The sensor window is arranged downstream of the light source, but may be considered arranged upstream of the detector. As the light source light propagates through the sensor window (in the direction of the skin), the sensor window is upstream of the sensor opening. Relative to the detector, the sensor window is downstream of the sensor opening (as light travels in the direction of the detector surface). During use, part of the light source light, passes through the sensor, through the sensor opening and is received at the skin. Hence, the skin receives unpolarized light source light via the sensor window. At least part of the light that is reflected at the skin passes through the sensor opening, the sensor window, optional optics, and is received at the detector surface.

Therefore, in yet a further aspect the invention also provides a method of sensing skin gloss, the method comprises providing light source light with the system as defined herein to a skin and sensing with the system the reflected light source light reflected at the skin.

The method is especially executed with the sensor on the skin, such as with a housing comprising an aperture on the skin, whereby during operation there is a second distance between the skin and the detector, or its last optics.

Especially, the method is a non-medical method. Especially, the method is a cosmetical method.

Also, in yet a further aspect the invention provides a data carrier having stored thereon program instructions, which when executed by the system as defined herein causes the system to execute the method as defined herein. For instance, to this end the system may comprise a processor.

As indicated above, the system may comprise a polarizer. The polarizer is configured to allow only one or more specific polarizations enter the detector. Hence, in specific embodiments the sensor comprises a polarizer configured upstream of the detector. Even more especially, the polarizer comprises one or more of (i) a segmented polarizer and (ii) a spatially varying polarizer. This allows a reduction of the influence of the (rotational) position of the detector, especially when the light sources are driven sequentially. In this way, the sensor may detect the reflected light as function of the light source. With the different polarizations of the polarizer, the sensitivity of the system may be higher. Especially, the polarizer is configured downstream of the sensor window. When a lens is available, the polarizer may be configured downstream of the lens (with the lens being configured upstream of the detector (surface). The polarizer thus especially receives reflected unpolarized light and transmits polarized right in the direction of the detector.

Therefore, in specific embodiments, the device comprises a sensing mode, wherein the light sources are configured to sequentially provide the light source light. In further specific embodiments, the detector may be configured to sequentially detect reflected light source light sequentially generated by the light sources, and configured to generate corresponding detector signals. As indicated above, the system further comprises an analysis system, with the analysis system being configured to generate a corresponding skin sensor value in dependence of a sensor signal of the sensor, and in specific embodiments wherein the skin sensor value is based on an average of respective detector signals.

In embodiments, the segmented polarizer comprises a pixelated wire grid polarizer with two or more pixels having different polarization orientations. Here, the term "pixels" may also refer to areas. Especially, the sensor comprises n light sources, such as four light sources, and wherein the segmented polarizer comprises a pixelated wire grid polarizer with n pixels having polarization orientations perpendicular to each other, such as two sets of two pixels (in the case of four light sources). As indicated above, the value of n is especially at least 2, such as 3 or 4, or more.

In embodiments, the spatially varying polarizer comprises one or more of an azimuthal varying polarizer and a radial varying polarizer, which especially allows more number of emitters to be configured very close to each other.

Best results may be obtained at about the Brewster angle. Hence, in embodiments the sensor is configured to provide the light source light with optical axes (OL) under an angle of incidence ($\alpha$) with the skin at a third distance (d3), wherein the angle of incidence ($\alpha$) is selected from the range of 50-60°, even more especially wherein the angle of incidence ($\alpha$) is selected from the range of 52-56°.

Hence, amongst others herein skin gloss measurement systems and methods using sequential illumination from multiple unpolarized light emitters illuminating the skin at an angle of incidence (essentially) equal to Brewster's or polarization angle and a segmented or spatially varying polarizer in the detection path are provided.

Especially good results may (thus) be obtained when the light sources are sequentially driven. As the light sources are configured at different positions, the reflection behavior and polarization behavior, as well as an angular dependency of the reflected light may in this way provide additional information (that may result from skin structure and/or, non-uniformity of illumination) and/or may allow reducing the dependence of the sensor on the rotational position on the skin.

Hence, in specific embodiments the device comprises a sensing mode, wherein the light sources are configured to sequentially provide the light source light.

For instance, the sensors may have a measuring frequency in the range of 0.1*n-100*n Hz, wherein n is the number of light sources. With for instance 1*n Hz, each second all light sources have been consecutively illuminated the skin and the detector has (consecutively) measured possible reflections based on the respective light sources.

Of course, the use of a plurality of light sources may also allow addressing of subsets of two or more light sources. For instance, it may also be possible when four light sources are used to have two sets of two light sources, which are configured opposite of each other (with the detector in between) which sets of light sources are alternatingly switched on and off.

Also combinations of such methods may be applied, wherein e.g. in time the composition of the set of light sources may change. For instance, in a mode during a predetermined time the light sources are addressed sequentially and in a subsequent predetermined time the light sources are addressed as a group. Such mode may include a repetition of these respective predetermined times. All kind of illumination schemes may be used to further create a more reliable measuring of the skin gloss.

The detector signal may be an average over the signals generated by the respective light sources. Hence, in yet further embodiments the detector is configured to sequentially detect reflected light source light sequentially generated by the light sources, and configured to generate corresponding detector signals, wherein the system further comprises an analysis system, wherein the analysis system is configured to generate a corresponding skin sensor value in dependence of a sensor signal of the sensor, and wherein the skin sensor value is based on an average of respective detector signals. Hence, especially the detector signals are first processed and then averaged. In this way the detector signal may be an average over the signals generated by the respective light sources.

As indicated above, the system may comprise at least three light sources. Yet further, as indicated above in embodiments the sensor has a sensor optical axis (O2), and wherein the light sources are configured rotationally symmetric around the sensor optical axis (O2).

In further specific embodiments, as also indicated above, the system may further comprise an analysis system wherein the analysis system is configured to generate a corresponding skin sensor value in dependence of a sensor signal of the sensor. There may be a number of ways in which the sensor signal is generated. Even though many low cost devices are reported for home-use applications, the gloss measurements using these devices appear not to be quantitative and also may not correlate with the subjective perception and reference device measurements. Methods for estimating the gloss may be based on counting the number of white pixels above a certain threshold in the camera images obtained using unpolarized illumination. However, it appears that the gloss estimation based on the number of white pixels depends on the incident light intensity levels (and its fluctuations), threshold and variation in the optical properties of skin (inter and intra-individual variations), which is less desirable.

Here below, some specific embodiments are described which may provide more reliable results.

Hence, in embodiments especially the system is configured to create an image of the skin with the detector, wherein the image of the skin comprises a first area wherein maximum intensity is sensed and a second area at a first image distance from the first area, wherein the first area and second area do not overlap, wherein the system is further configured to generate the skin sensor value based on an intensity dependent of the reflected light source light along a path between the first area and the second area. The image may have an image area. The first and the second area may be areas of e.g. 0.05-30%, such as 0.05-15%, like 0.1-10% of the image area. Further, first image distance, i.e. the distance between the first area and second area, more precisely the shortest distance between the boundaries of these two areas, may be in the order of at least the area size of the first area or the second area. In general, the first area and second area may be essentially the same. Optionally, the areas may also be different but then a correction factor may be applied. Further, in general these areas are chosen square or rectangular, especially square. The area wherein a maximum intensity is sensed may be the area of the image where essentially specular reflection takes place, i.e. where the light source light is minor like reflected and detected by the detector.

Hence, the first image distance may be in the range the square root of 0.05-30% of the image area, such as the square root of 0.05-15% of the image area, like the square root of 0.1-10% of the image area. Especially, the distance between the first area and the second area is at least 5% of the square root of the image area. Note that the image area may not have a fixed value, but may e.g. depend upon the magnification.

Further, note that the term "creating an image" and similar terms may not necessarily include the creation of a real image at a moment in time but may also refer to reading out the values of the detector at different positions over the detector surface.

It appears that information that can be derived from the two areas and/or from a (straight) line or the area in between those two areas can provide information over the glossiness, which may allow quantifying of the skin gloss (including skin oiliness), especially when the system has been calibrated (see also below).

Therefore, in embodiments the system may be configured to generate the skin sensor value based on a slope of a curve defined by the intensity of the reflected light source light along the path between the first area and the second area. Hence, based on the slope of the curve or an angle of the curve, it appears that useful skin gloss values can be generated.

Alternatively or additionally, the system may be configured to generate the skin sensor value based on an area below a curve defined by the intensity of the reflected light source light along the path between the first area and the second area. Hence, also based on the area under the curve or an angle of the curve, it appears that useful skin gloss values can be generated. The path can also be indicated as a straight trajectory or line.

Yet alternatively or additionally, the system may be configured to generate the skin sensor value based on a number of pixels of the image above a predefined threshold. Hence, based on the number of pixels above threshold also it appears that useful skin gloss values can be generated.

Further, alternatively or additionally, the system may be configured to generate the skin sensor value based on an average number of pixels of the image above predefined thresholds weighted with the corresponding pixel intensity, respectively. Therefore, also based on the weighted number of pixels above threshold useful skin gloss values can be generated.

Yet, alternatively or additionally the system may be configured to generate the skin sensor value based on a relation between an integrated intensity of the first area and the second area. Therefore, also the ratio specular to diffuse intensity of these respective ratios may be used for generating skin gloss values. For instance, when the system is calibrated with an essentially specularly reflective area and with an essentially diffuse reflective area, skin gloss parameters can be derived from the ratio specular to diffuse intensity of these respective ratios.

Further, alternatively or additionally, system is configured to define binary large objects ("blob") in the image, and wherein the system is configured generate the skin sensor value based on or more of average size and maximum size of the binary large objects in the image. Hence, based on the number of blobs and/or sizes of the blobs also useful skin gloss values can be generated. Hence, in this embodiment is not the number of white pixels is used per se, but blobs are defined. Hence, also a threshold may be defined for those blobs, like at least k number of adjacent pixels over a specific intensity threshold value.

In above-mentioned embodiments, a number of times calibration has been mentioned. Especially for a quantitative evaluation of the skin gloss or skin oiliness, a calibration of the system, more precisely of the sensor (and in fact thus the detector) may be useful. This calibration can be done after production of the sensor. Alternatively or additionally, the calibration may software implemented for each sensor based on one or more earlier calibrations of example sensors. Calibration may also be part of a measuring process or may be regularly scheduled. In a specific embodiment, calibration is applied once after production of the sensor. Further, the system may include control routines that may update the calibration on the basis of sensor parameters of a reference sensor or based on e.g. drift in the signal, etc. etc.

In specific embodiments, the system is configured to generate a corresponding skin sensor value in dependence of a sensor signal of the sensor after a flat-field correction. Flat-field correction is a technique used to improve quality in digital imaging. Flat-field correction is especially used to compensate for the artifacts from 2-D images that are caused by non-uniformity of illumination and detection, variations in the pixel-to-pixel sensitivity of the detector and/or by distortions in the optical path. As indicated above, the flat-field correction may be based on a measurement with purely diffuse reference, such as e.g. diffuse standard like Spectralon. Based on such measurements, a flat-field correction may be provided, which may be used in any measurement (as herein described).

In yet further embodiments, the system is configured to generate a corresponding skin sensor value in dependence of a sensor signal of the sensor based on an average of the respective signals of red, green, and blue channels of the detector.

BRIEF DESCRIPTION OF THE DRAWINGS

Embodiments of the invention will now be described, by way of example only, with reference to the accompanying schematic drawings in which corresponding reference symbols indicate corresponding parts, and in which.

The schematic drawings are not necessarily to scale.

DETAILED DESCRIPTION OF THE EMBODIMENTS

Figure 1A:
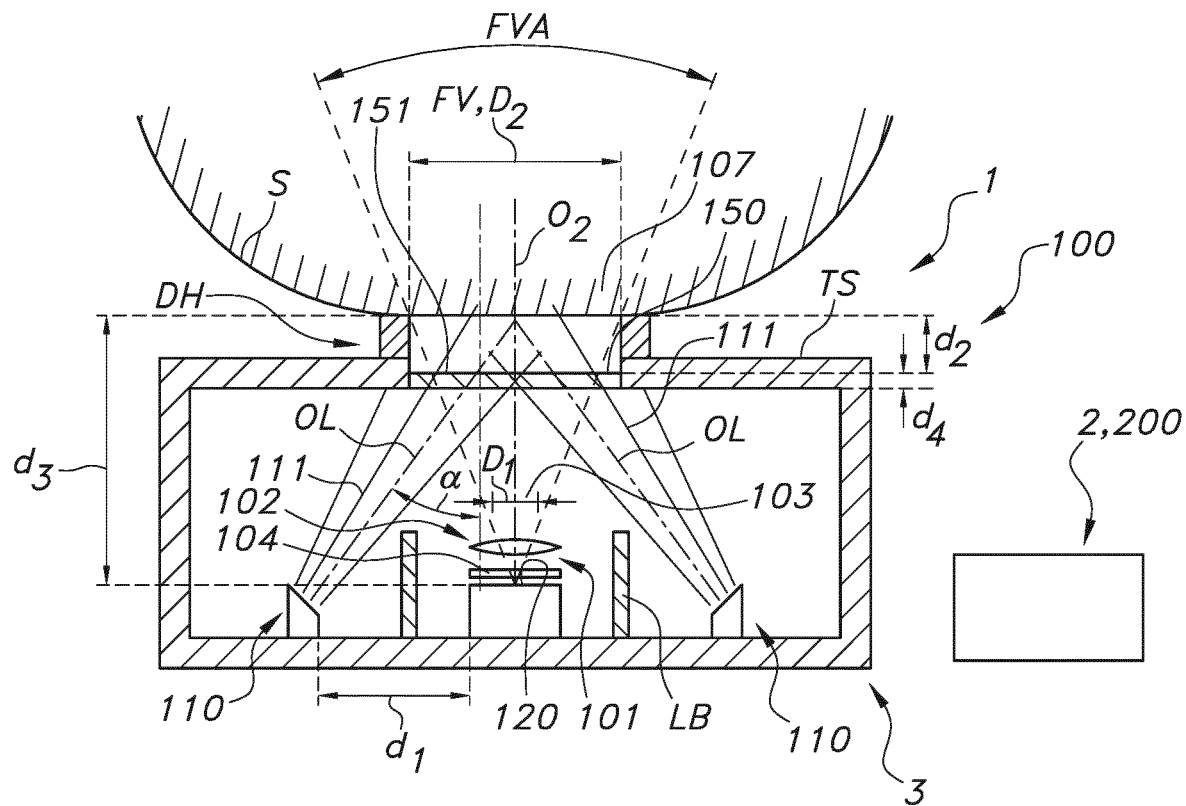
FIGS. 1a-1b schematically depict some aspects of the system.

FIG. 1a schematically depicts a system 1 comprising a sensor 100 for measuring a skin parameter (selected from one or more of the group consisting of skin gloss and skin oiliness). The sensor 100 comprises a plurality of spatially separated light sources 110 configured to provide light source light 111, and a detector 120 configured at a first distance d1 from each of the light sources 110. The sensor 100 may especially be configured to provide the light source light 111 with optical axes OL under an angle of incidence a selected from the range of 10-80° with the skin at a third distance d3 and to detect reflected light source light 111. The sensor 100 may especially comprises at least three light sources 110 here, only two are depicted for the sake of understanding, wherein the light sources 110 are configured to provide unpolarized (visible) light source light 111. The first distance d1 may e.g. be selected from the range of 10-80 mm, and wherein the detector 120 is configured to detect polarized light. The dashed line S indicates the skin. Reference 150 indicates a sensor window and reference 151 indicates the sensor window material. The sensor window 150 has a sensor window thickness d4, e.g. selected from the range of 0.1-20 mm.

The detector 120 may e.g. comprise a 2D camera 101. Further, the sensor 100 may comprise a focusing lens 102 configured upstream of the detector 120, and an aperture 103 configured upstream of the detector 120 and upstream of the focusing lens 102 (and downstream of the sensor window 150). The aperture 103 has—in embodiments—a diameter D1 selected from the range of 0.1-0.8 mm. The focusing lens may e.g. be an f 5-15 mm, like 10 mm lens. Further, the system may include a second focusing lens, the combination of this lens with the first lens may provide a desired field of view and depth of focus for the overall system (see e.g. FIG. 1A). The light sources 110 are configured to provide unpolarized white light source light 111.

As indicated in FIG. 1a, the system 1 may further comprise an analysis system 2 wherein the analysis system 2 is configured to generate a corresponding skin sensor value in dependence of a sensor signal of the sensor 100.

The analysis system 2 may be comprised by a device that also comprises the sensor 100 (see also FIG. 1b), or may be comprised by a separated device. FIG. 1a also schematically depicts such embodiment, wherein the system 1 comprises the a skin care device 3, wherein the skin care device 3 comprises the sensor 100, and a second device 200 functionally coupled to the skin care device 3, wherein the second device 200 comprises the analysis system 2.

The sensor 100 includes an opening 107. This opening may especially be flat, i.e. its circumference may have an edge that is essentially flat. In this way, the sensor may be configured flat on the skin. The opening 107 may have a diameter D2 or equivalent diameter D2 which may be in the range of about 10-30 mm.

Reference O2 refers to the optical axis of the sensor 100. When the sensor 100 is configured on the skin, this axis may essentially coincide with a normal to the skin.

Reference TS indicates a top surface of the sensor. This may be a planar surface. Reference LB indicates a direct light blocker, configured to prevent that light of the light sources may reach the detector without a single reflection and/or which may reduce light reaching the detector 120 that has not been reflected by the skin but by other internal surfaces of the sensor. Reference 104 refers to a polarizer.

The axis O2 may essentially coincide with a normal to the skin.

Especially, TS may indicate a top surface of a housing 105. The top surface TS may in fact define the second distance d2 from the skin to the detector 120 or its last lens. Here, the top surface TS comprises aperture 107. The opening size of the aperture can also be indicated as field of view (FOV). The field of view is herein also indicated with reference FV. The field-of-view (FOV) may be defined as the range of angles from which the incident radiation can be collected by the detector. Note that the opening or housing aperture 107 may be circular, but may also be square or rectangular, or may have another shape. Reference FVA indicates the field of view angle. Reference TT indicates the total track, which is the distance from the aperture 107 (i.e. skin during operation) and the top side of a support hosting the light source 110, which distance is essentially the same as the distance to the top of the light source 110, as in general solid state light sources, such as LEDs, are applied. The total track may be in the range of 10-200 mm, such as in the range of range of 10-80 mm, such as e.g. in the range of 10-30 mm, or in the range of 40-200 mm, like in the range of 40-80 mm. The total track TT is larger than the second distance d2. The detector 120 and optional optics may have a height in the range of about 1-50 mm, such as 1-20 mm. As can be derived from the drawing, when the sensor 100 is configured on the skin, the second distance d2 is guaranteed. Therefore, the sensor 100 may include a distance holder, such as a housing 105 (as depicted), or optionally a housing and a separate distance holder. As indicated above, the visible light source light 111 is especially unpolarized. Hence, the light source light 111 is especially unpolarized light source light. Note that the optical axis O2 of the sensor 100 and an optical axis of the detector 120 may essentially coincide. Further, the optical axis O2 of the sensor and a net optical axis of all light sources 110 may coincide.

In general, distance d2 may be defined as the distance between an aperture that is to be positioned on the skin, and the detector, or its last optics, seen from the detector.

Referring to FIG. 1a (and also FIG. 5), the light sources are not directly behind the sensor window or behind the opening 107. Hence, especially a distance between the light source and the optical axis O2 of the sensor is larger than a distance of an edge of the sensor window 150 to the optical axis O2. Likewise, especially a distance between the light source and the optical axis O2 of the sensor is larger than a distance of an edge of the opening 107 to the optical axis O2. In specific embodiments, a distance between the light source and the optical axis O2 of the sensor is larger than half an equivalent diameter of the sensor window 150. In other specific embodiments, a distance between the light source and the optical axis O2 of the sensor is larger than half an equivalent diameter of the opening 107. Note that in the herein schematically depicted embodiments, the distance of an edge of the opening 107 to the optical axis O2 will (in general) be (essentially) identical to the distance between an edge of the sensor window 150 to the optical axis O2.

Figure 5:
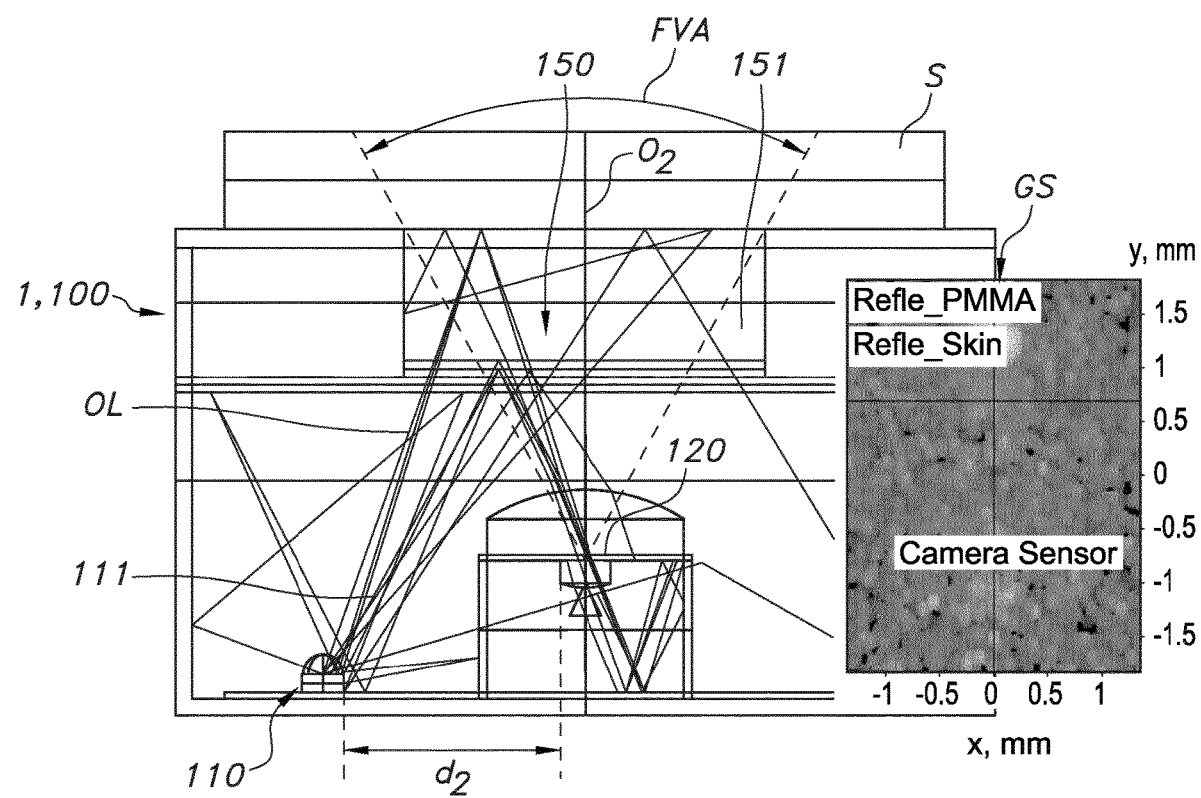
FIG. 5: Simulations showing the schematic representation of the prototype using a glass window at a distance more than 3 mm from the skin (Left). Reflected spot from the PMMA window and skin are on the sensor (Right)

The optical axis of the light source may be defined as the optical axis of the beam of light source light that may escape from the opening 107. As can be seen in FIGS. 1a and 5, this beam may have another shape then the beam generated by the light source, as part of the light may be reflected at the housing, and optionally after (multiple) reflections also exit via the opening 107.

The distance d2 and the thickness d4 of the sensor window is especially positioned and calculated in such a way to avoid direct specular reflections from the sensor window to the detector.

Figure 1B:
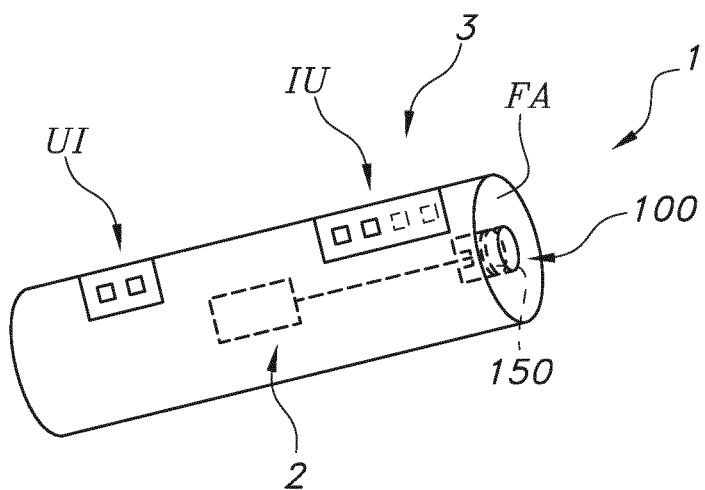

FIG. 1b schematically depicts an embodiment of the system 1, wherein the system 1 comprises a skin care device 3, such as skin cleansing device, skin rejuvenation device, wherein the skin care device 3 comprises the sensor 100 and the analysis system 2. The skin care device 3 may comprise an indication unit IU and/or also a user interface UI. Reference FA indicates a functional area, such as an area that may be used for massaging or exfoliating the skin.

Figure 2:
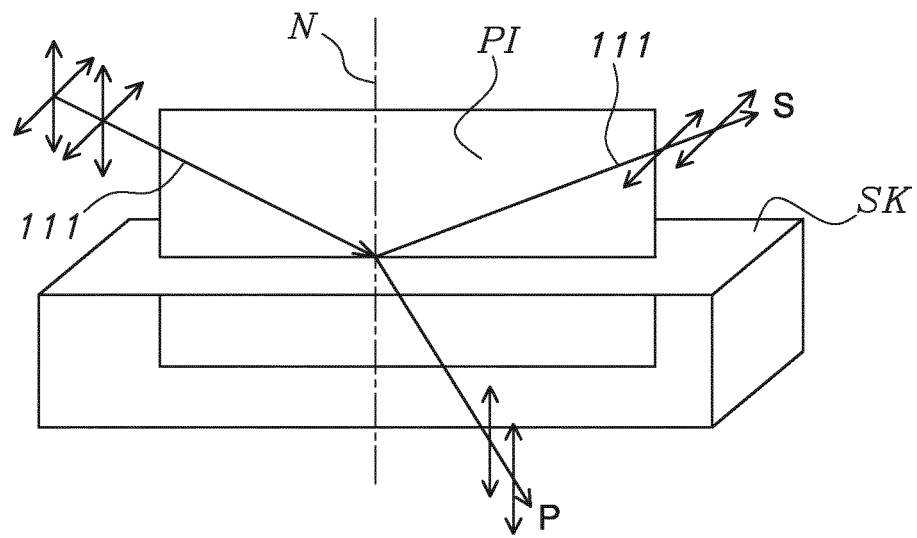
FIG. 2: Reflection and transmission of unpolarized light at an interface.

When unpolarized light is reflected by a skin surface, the polarization properties of the reflected light depends on the angle of illumination (FIG. 2). The two orthogonal linear polarization states important for reflection and transmission are referred to as p- and s-polarization. P-polarized (from the German parallel) light has an electric field polarized parallel to the plane of incidence, while s-polarized (from the German senkrecht) light is perpendicular to this plane. Reference N indicates the normal (to a surface), reference PI indicates a plane of incidence. Further, reference SK indicates an incident surface, such as a skin surface. References S and P indicate the polarizations.

The reflected light will be unpolarized for angle of illumination equals to 0° or 90°, partially polarized (preferably S) for angles of illumination in between 0° and 90°, and plane polarized (S) for one angle of illumination equals to the polarization angle or Brewster's angle.

The angle of incidence (0° and 90°) at which the reflection coefficient for light which has electric field parallel to the plane of incidence (P) goes to zero and the reflected light at that angle is linearly polarized with its electric field vectors perpendicular to the plane of incidence (S) is called the polarizing angle or the Brewster angle. The polarizing angle or the Brewster angle ($\theta B$) can be calculated based on the Fresnel's equations. The Fresnel equations predict that light with the p polarization (electric field polarized in the same plane as the incident ray and the surface normal) will not be reflected if the angle of incidence is $\theta_B = 1/\tan(n_2/n_1)$, wherein $n_1$ is the refractive index of the initial medium through which the light propagates (the "incident medium"), and $n_2$ is the index of the other medium. For a glass medium ($n_2 \approx 1.5$) in air ($n_1 \approx 1$), Brewster's angle for visible light is approximately 56°. For the optical lay-out as disclosed in this invention, the light is incident at the air-skin interface and the Brewster's angle is approximately 54°. The preferred range is 50-60°).

Therefore, in embodiments a segmented (for lower number of emitters up to four to eight) or spatially varying polarizer (for higher number of emitters for instance above 12) in the detection path can be used. Especially, the number of segments equals to the number of emitters.

When the angle of illumination is between 0-90°, the detection of partially polarized (preferably S) reflected specular light which is a measure of gloss can be enhanced by filtering in this component using an S polarizer before the camera. In the case of illumination scheme using multiple light sources, segmented polarizer or spatially varying polarizer can be used.

Hence, amongst others, it is herein proposed to use camera systems and methods for quantitative measurement of skin gloss that is (are) less dependent on the rotation angle of the sensor. The proposed invention—may in embodiments amongst others—be based on using sequential illumination from more than three light sources (unpolarized illumination) and sequential detection using a single low cost camera sensor (polarized detection). The gloss value is estimated based on the average number of pixels estimated from the multiple independent images taken along different directions. The schematic representation of the optical lay-out of the camera prototype are shown in FIG. 1. The image processing method (algorithms) used for estimating the gloss value can be either based on the number of white pixels or the slope of the intensity variation along the optical axis normalized to the maximum value after flat-field correction, though other options may also be possible (see also below).

Figure 3:
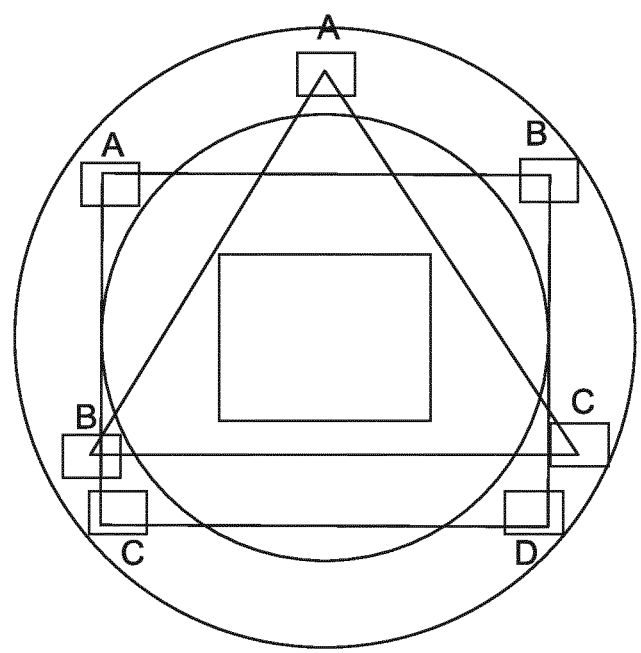
FIG. 3: Schematic representation of a possible polarization scheme for illumination and detection.

Based on the experimental data measured on Spectralon, ex-vivo skin and in-vivo we exemplify that the underestimation of the gloss content resulting from the rotation related effects associated with the use of using single emitter could be minimized by using sequential illumination employing more than three emitters (triangular configuration for N=3 and rectangular configuration for N=4 etc.) that are symmetrically placed in a ring illumination configuration (FIG. 3). When multiple emitters are used simultaneously, the gloss value depends on the rotation angle, effect predominantly contributed by the number of white pixels in the regions where the intensity distributions from multiple emitters overlap. Herein, A, B, and C indicate light sources, which are arranged in a ring configuration.

For home use applications, in particular in an environment like bathroom, the sensor is expected to be water proof and contamination free. This can be realized by using a transparent glass window that shields the whole illumination and detection optics. Typically, in skin sensors such as dermatoscopes, a glass window is placed in contact with the skin. However, when a glass window is used in contact with the skin, the sensor signal will be dominated by the 'ghost spot' arising from the Fresnel reflections of the two interfaces of the glass window (air-glass and glass-air interfaces). This ghost spot does not carry any information from the sample (skin) and this is what we call as "unwanted reflections". For a given illumination conditions, the ghost spot is expected to be more intense than the light reflected from the skin because of the higher reflection coefficient of the glass-air interface compared to the effective reflection resulting from the skin. In addition to this, the ghost spot from the glass can interfere and may overlap with the signal coming from the skin resulting in poor estimation of skin oil/gloss content.

Figure 4A:
FIG. 4a: Measurement on skin using an exit glass window in contact with skin. Ghost spot from the glass window is more intense than the light intensity detected from the skin and therefore it is not a possible solution.

The following solutions were tested to solve this issue arising from the ghost spot:

1. Glass window on the top of sensor in contact with skin (FIG. 4*a*):

2. Angled window: This solution may work in a sensor which uses one or two emitters where the tilt can be optimized for two emitters. However, this solution is not optimal in a system using more than three emitters for illumination.

Figure 4B:
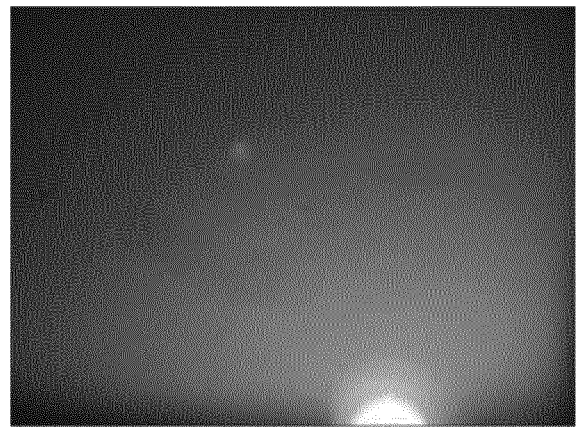
FIG. 4b: Antireflection coated Glass window between optics and glossy paper. Specular reflections are reflected away, however image looks green due to the dependence of angle of incidence and wavelength selectivity on di-electrical coatings.

3. Antireflection coating: Anti-reflection coating does not work at these broad range of illumination angles and in particular in combination with a broadband light source (FIG. 3). An AR coated (dielectrical coating) glass was used on a high gloss paper to test whether the ghost specular reflection is out of the sensor. We observe that because of the wavelength cut-off frequency (normally about 700 nm) sensitivity of the sensor will shift to lower wavelengths and will decrease red sensitivity and the resulting images (FIG. 4*b*) will look greenish and therefore is not a potential solution for this problem.

Figure 6:
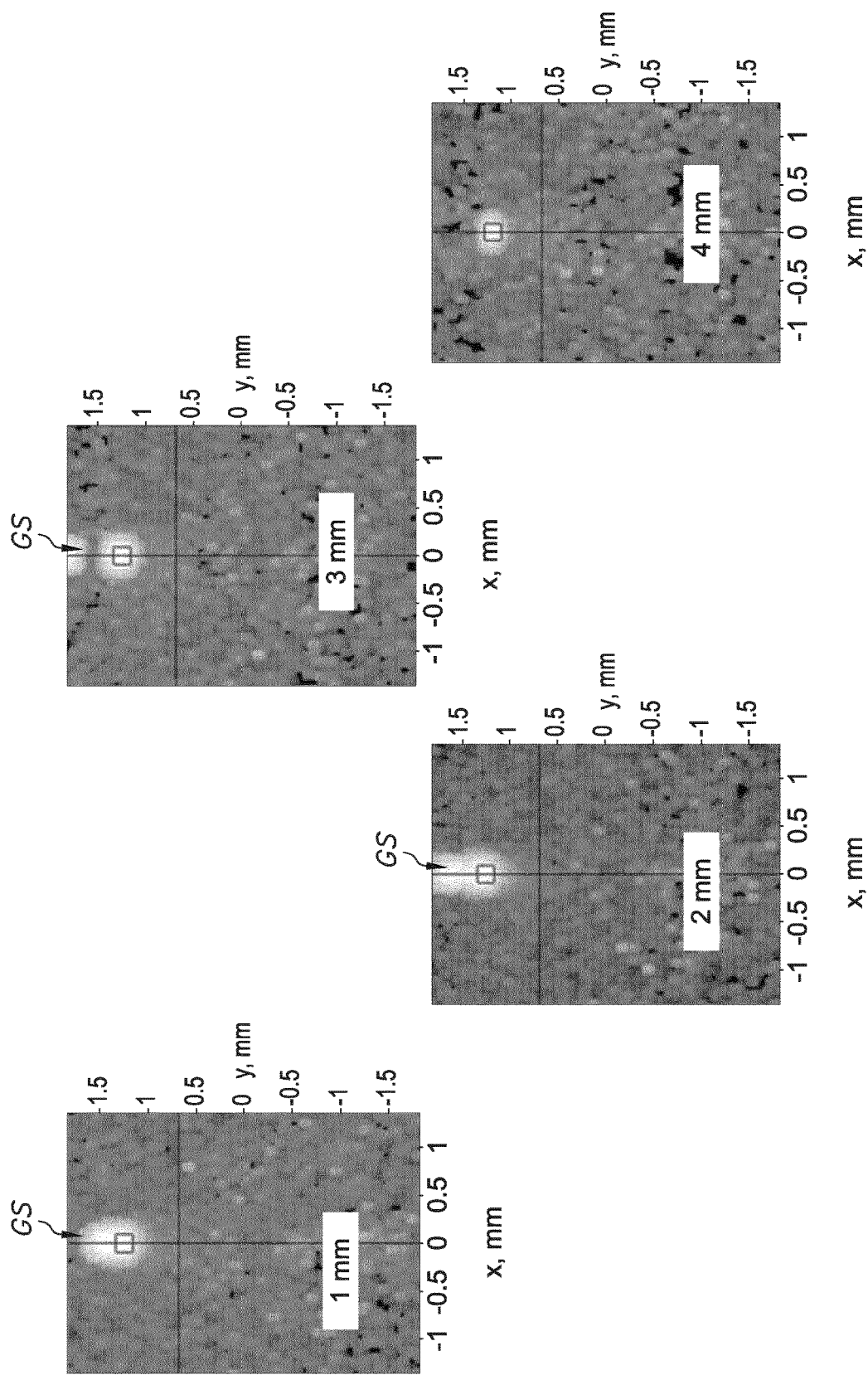
FIG. 6: simulations showing the shifting of the reflected spot (Ghost spot) from the PMMA window on the sensor with respect to the spot reflected from the skin.

Amongst others, this invention proposes a low cost waterproof and contamination-free sensor for measuring skin characteristics. The proposed invention is based on using a transparent window, preferably with a thickness of more than 3 mm and at a distance of few mm, preferably more than 3 mm from the skin. This solution makes the Fresnel reflection (unwanted ghost spot (indicated in FIG. 5 with reference GS)) from the window to be off the sensor compared to the reflected intensity from the skin (FIG. 5). In a preferred embodiment, the transparent window use a roughened surface so that Fresnel reflected light from the air-glass interface is distributed over a range of angles so that the effective impact resulting from the ghost spot is significantly reduced. The Simulations calculate the photometric and radiometric quantities to perform a complete illumination and detection analysis. The optical layout of the system used in the simulations were based on the configuration of the prototype developed for oil/gloss measurements. The schematic representation of the camera prototype and system layout used in the simulations are shown in FIG. 5. Results as function of the distance of the window to the skin are depicted in FIG. 6. It is clear that the ghost spot GS moves away from the spot reflected from the skin with increasing distance of the window from the skin.

Figure 7:
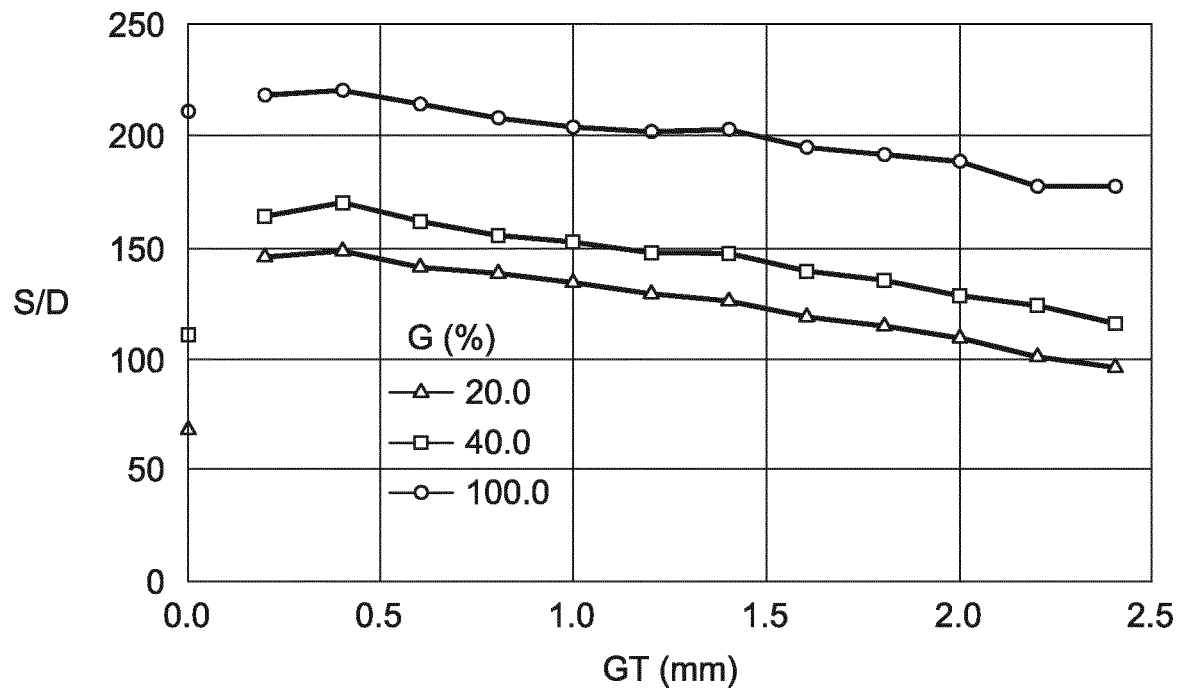
FIG. 7: The dependence of S/D ratio (specular/diffuse) on the glass thickness (GT) of glass window (range from 0-3 mm) and for different gloss values (Gloss~20, 40, 100 a.u.). reference G indicates the glossiness in % (20, 40 and 100%); The distance of the glass window from the skin was 0.1 mm. For the sample with gloss value of 20%, gloss value in the range relevant for skin, use of thick glass window can minimize the effect of ghost spot. At glass thickness 0 mm, there is (thus) no sensor window.
Figure 8:
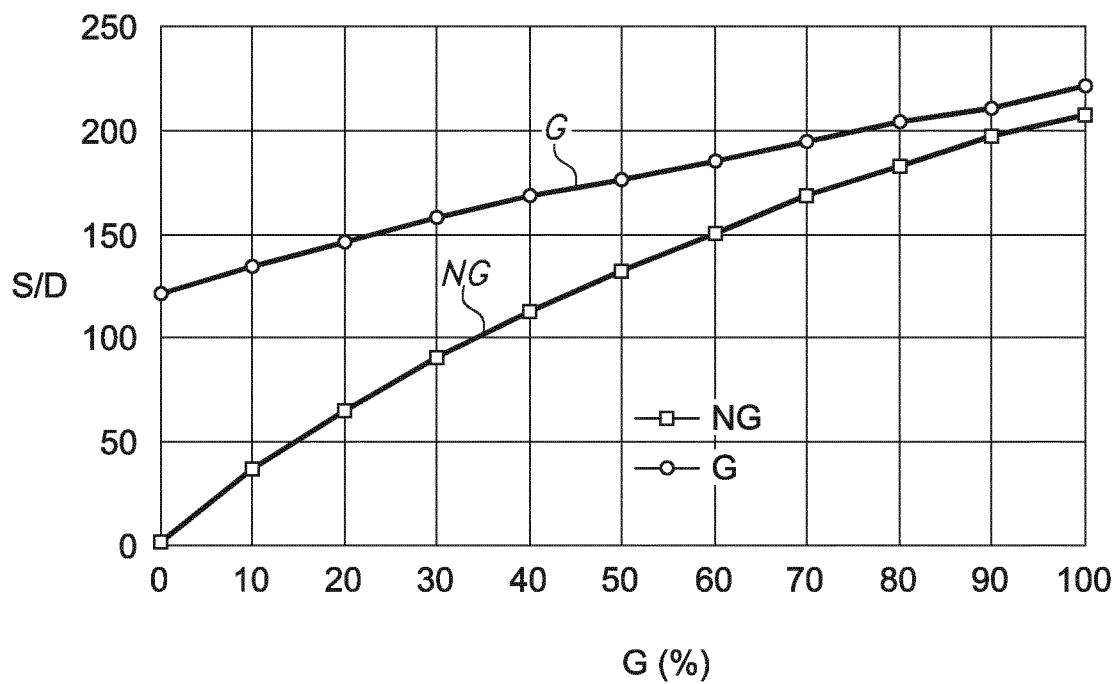
FIG. 8: The dependence of S/D ratio on the gloss value of the sample (Gloss~0 to 100 a.u.). The distance of the glass window from the skin was 0.1 mm. The influence of ghost spot is more critical for low gloss samples and the gloss value of skin is expected to be in this range (~10-20% Gloss units). Here, reference G indicates the device including a glass window, and reference NG indicates the device without such glass window. Further, G on the x-axis indicates the glossiness (%)
Figure 9:
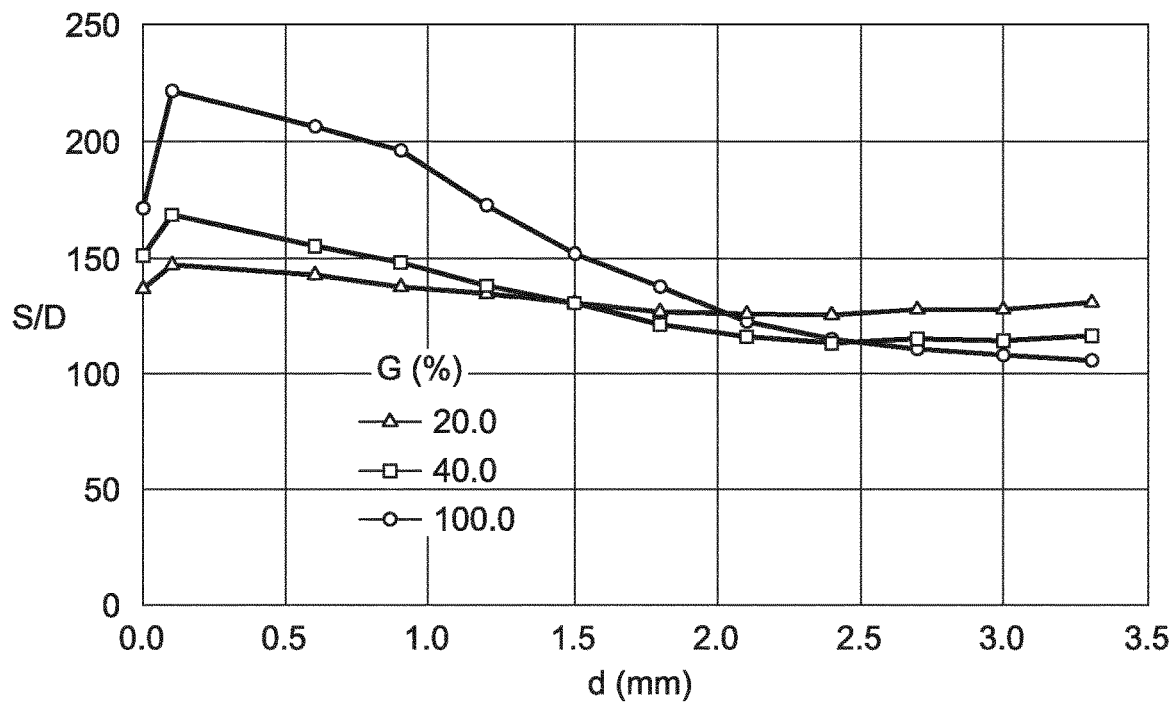
FIG. 9: The dependence of S/D ratio on the gloss value of the sample (Gloss~0 to 100 a.u). The influence of ghost spot is less critical for all gloss samples when the distance from the skin is more than 2 mm; reference G indicates again the glossiness (%), which are 20, 40, and 100%, respectively. Further, d on the x-axis indicates the distance (mm) between skin and window.

The intensity distribution on the camera sensor and the corresponding intensity plot obtained for samples with different gloss values are shown for different configurations FIGS. 7-9. The ratio of specular to diffuse intensity was estimated as a function of following parameters: thickness of the glass window, distance from the skin, and samples with a range of gloss values (Mirror (Gloss~100 a.u)) to diffuse standard (Gloss~0 a.u).

Figure 10:
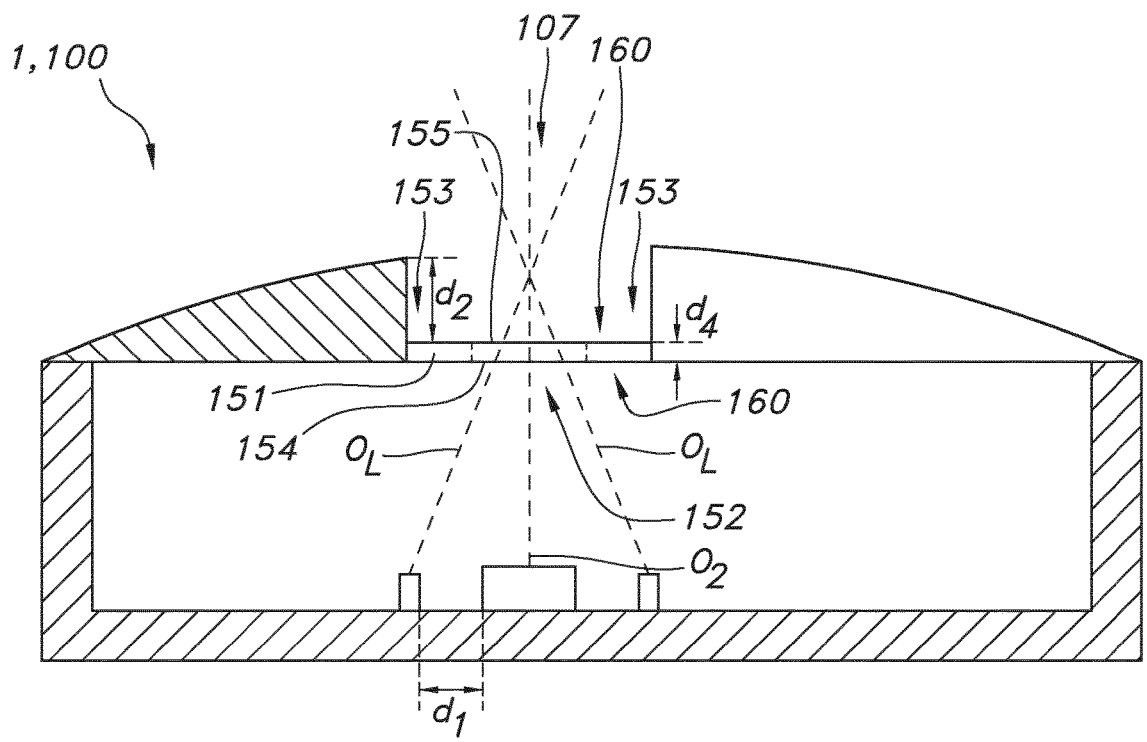
FIG. 10 schematically depicts a further embodiment.

FIG. 10 schematically depicts an embodiment wherein the sensor window 150 comprises a central part 152 and a peripheral part 153. The optical axis O2 of the detector 120, and the optical axes OL of the light source light, passes through the central part 152. The peripheral part 153 comprises antiglare elements 160. The central part does essentially not comprise such antiglare elements. The sensor window 150 comprises an upstream face 154 and a downstream face 155. One or more of the upstream face 154 and the downstream face 155 in the peripheral part 153 may have such antiglare elements, especially having a root mean square surface roughness selected from the range of 40-500 nm.

The term "plurality" refers to two or more.

The term "substantially" herein, such as in "substantially consists", will be understood by the person skilled in the art. The term "substantially" may also include embodiments with "entirely", "completely", "all", etc. Hence, in embodiments the adjective substantially may also be removed. Where applicable, the term "substantially" may also relate to 90% or higher, such as 95% or higher, especially 99% or higher, even more especially 99.5% or higher, including 100%. The term "comprise" includes also embodiments wherein the term "comprises" means "consists of". The term "and/or" especially relates to one or more of the items mentioned before and after "and/or". For instance, a phrase "item 1 and/or item 2" and similar phrases may relate to one or more of item 1 and item 2. The term "comprising" may in an embodiment refer to "consisting of" but may in another embodiment also refer to "containing at least the defined species and optionally one or more other species".

Furthermore, the terms first, second, third and the like in the description and in the claims, are used for distinguishing between similar elements and not necessarily for describing a sequential or chronological order. It is to be understood that the terms so used are interchangeable under appropriate circumstances and that the embodiments of the invention described herein are capable of operation in other sequences than described or illustrated herein.

The devices herein are amongst others described during operation. As will be clear to the person skilled in the art, the invention is not limited to methods of operation or devices in operation.

It should be noted that the above-mentioned embodiments illustrate rather than limit the invention, and that those skilled in the art will be able to design many alternative embodiments without departing from the scope of the appended claims. In the claims, any reference signs placed between parentheses shall not be construed as limiting the claim. Use of the verb "to comprise" and its conjugations does not exclude the presence of elements or steps other than those stated in a claim. Unless the context clearly requires otherwise, throughout the description and the claims, the words "comprise", "comprising", and the like are to be construed in an inclusive sense as opposed to an exclusive or exhaustive sense; that is to say, in the sense of "including, but not limited to". The article "a" or "an" preceding an element does not exclude the presence of a plurality of such elements. The invention may be implemented by means of hardware comprising several distinct elements, and by means of a suitably programmed computer. In the device claim enumerating several means, several of these means may be embodied by one and the same item of hardware. The mere fact that certain measures are recited in mutually different dependent claims does not indicate that a combination of these measures cannot be used to advantage.

The invention also provides a control system that may control the apparatus or device or system, or that may execute the herein described method or process. Yet further, the invention also provides a computer program product, when running on a computer which is functionally coupled to or comprised by the apparatus or device or system, controls one or more controllable elements of such apparatus or device or system.

The invention further applies to a device comprising one or more of the characterizing features described in the description and/or shown in the attached drawings. The invention further pertains to a method or process comprising one or more of the characterizing features described in the description and/or shown in the attached drawings.

The various aspects discussed in this patent can be combined in order to provide additional advantages. Further, the person skilled in the art will understand that embodiments can be combined, and that also more than two embodiments can be combined. Furthermore, some of the features can form the basis for one or more divisional applications.

The invention claimed is:

1. A system comprising a sensor for measuring a skin parameter of skin, the sensor comprising:
    (i) at least three spatially separated light sources configured to provide unpolarized light source light;
    (ii) a detector arranged a first distance from each of the light sources, wherein the first distance is in a range of 5-80 mm;
    (iii) a sensor opening configured downstream of the light sources for propagation of the light source light out of the sensor to the skin, and upstream of the detector for entrance of reflected sensor light from the skin into the sensor; and
    (iv) a sensor window, formed of a material transmissive for the light source light, configured downstream of the light sources and upstream of the sensor opening with respect to the light source light, and configured upstream of the detector with respect to the reflected light, wherein a second distance between the sensor window and the sensor opening is at least 3 mm.

2. The system according to claim 1, wherein the second distance is at least 4 mm.

3. The system according to claim 1, wherein the second distance is selected from is in a range of 4-10 mm, wherein the sensor opening has an equivalent circular diameter in a range of 1-20 mm, and wherein the sensor window has a sensor window thickness in a range of 0.1-20 mm.

4. The system according to claim 1, wherein the first distance is in a range of 8-14 mm, and wherein an angle of incidence is in a range of 20-60°.

5. The system according to claim 1, wherein the material is selected from a group consisting of glass and poly methyl methacrylate.

6. The system according to claim 1, wherein the sensor window comprises a central part and a peripheral part, wherein an optical axis of the detector passes through the central part, and wherein the peripheral part comprises antiglare elements.

7. The system according to claim 6, wherein the sensor window comprises an upstream face and a downstream face, wherein one or more of the upstream face and the downstream face in the peripheral part has a root mean square surface roughness in a range of 40-500 nm.

8. The system according to claim 6, wherein the sensor window comprises surface features, wherein the surface features have an average cross-sectional equivalent circular diameter selected in a range of 40 nm-100 µm, and wherein an average distance between neighboring surface features is equal to or less than five times the average cross-sectional equivalent circular diameter.

9. The system according to claim 1, wherein the sensor further comprises a polarizer configured upstream of the detector, wherein the polarizer comprises one or more of a segmented polarizer and a spatially varying polarizer, and wherein the detector is configured to detect polarized light form the polarizer.

10. The system according to claim 1, wherein the detector comprises a 2D camera, wherein the sensor further comprises a focusing lens configured upstream of the detector, and an aperture configured upstream of the detector and upstream of the focusing lens, and wherein the aperture has a diameter in a range of 0.1-0.8 mm.

11. The system according to claim 1, wherein the system further comprises an analysis system wherein the analysis system is configured to generate a corresponding skin sensor value in dependence of a sensor signal of the sensor.

12. The system according to claim 11, wherein the system comprises a sensing mode, wherein the light sources are configured to sequentially provide the light source light, wherein the detector is configured to sequentially detect reflected light source light sequentially generated by the light sources, and configured to generate corresponding detector signals, and wherein the skin sensor value is based on an average of respective detector signals.

13. The system according to claim 1, wherein the sensor has a sensor optical axis, and wherein the light sources are configured rotationally symmetric around the sensor optical axis, and wherein the sensor is configured to provide the light source light with optical axes under an angle relative to the sensor optical axis of the detector selected from a range of 10-80°.

14. The system according to claim 1, wherein the sensor window is planar with no optical function of converging or diverging light rays.

15. The system according to claim 1, wherein a distance between the sensor window and the sensor opening and a thickness are selected to avoid direct specular reflections from the sensor window to the detector.

16. A sensor for measuring a skin parameter of skin, the sensor comprising:
    at least three spatially separated light sources configured to provide unpolarized light source light;
    a detector arranged an equal distance from each of the light sources;
    a sensor opening configured to output the light source light provided by the light sources to illuminate a section of the skin, and to input reflected sensor light reflected from the section of the skin in response to the light source light to the detector for detecting the reflected sensor light; and
    a sensor window arranged between the sensor opening and each of the three light sources and the detector, and offset from the sensor opening by a second distance, wherein the sensor window is formed of a material transmissive for passing the light source light from the at least three light sources to the sensor opening and for passing the reflected sensor light from the sensor opening to the detector.

17. The sensor according to claim 16, wherein the sensor window comprises a central part and a peripheral part, wherein an optical axis of the detector passes through the central part, and wherein the peripheral part comprises antiglare elements.

18. The sensor according to claim 16, wherein the sensor window is planar with no optical function of converging or diverging light rays.

19. The sensor according to claim 16, further comprising a housing containing at least the light sources and the detector, and having an aperture corresponding to the sensor opening, wherein the sensor window encloses the light sources and the detector in the housing.

* * * * *